(12) United States Patent
Grenier et al.

(10) Patent No.: US 11,729,895 B2
(45) Date of Patent: Aug. 15, 2023

(54) METHODS AND APPARATUS FOR CONTROL OF RADIOGRAPHIC SOURCE EXPOSURE

(71) Applicant: Illinois Tool Works Inc., Glenview, IL (US)

(72) Inventors: Steven J. Grenier, Arlington, MA (US); John H. Crosby, Jr., Concord, MA (US); Curtis D. Auzenne, Prairieville, LA (US)

(73) Assignee: Illinois Tool Works Inc., Glenview, IL (US)

( * ) Notice: Subject to any disclaimer, the term of this patent is extended or adjusted under 35 U.S.C. 154(b) by 113 days.

(21) Appl. No.: 17/500,617

(22) Filed: Oct. 13, 2021

(65) Prior Publication Data
US 2022/0132646 A1   Apr. 28, 2022

Related U.S. Application Data (60) Provisional application No. 63/106,664, filed on Oct. 28, 2020.

(51) Int. Cl.
*H05G 1/38* (2006.01)
*H05G 1/08* (2006.01)
*H05G 1/04* (2006.01)

(52) U.S. Cl.
CPC .................. *H05G 1/38* (2013.01); *H05G 1/04* (2013.01); *H05G 1/085* (2013.01)

(58) Field of Classification Search
CPC ........... H05G 1/04; H05G 1/38; H05G 1/085; H05G 1/02; H05G 1/30; H05G 1/06; H05G 1/025; A61B 6/107; A61B 6/40; A61B 6/4258; A61B 6/06; A61B 6/482; A61B 6/4405; A61B 6/4411; A61B 6/467;

(Continued)

(56) References Cited

U.S. PATENT DOCUMENTS

| 4,314,157 A | 2/1982 | Gaines |
| 2017/0215977 A1* | 8/2017 | Saraliev ................. A61B 34/37 |
| 2019/0267146 A1 | 8/2019 | Dicharry |

FOREIGN PATENT DOCUMENTS

| GB | 2061080 | 5/1981 |
| GB | 2251047 A * | 6/1992 ............. G01N 23/22 |

OTHER PUBLICATIONS

Int'l Search Report and Written Opinion Appl No. PCT/US2021/056430 dated Feb. 2, 2022.

* cited by examiner

*Primary Examiner* — Irakli Kiknadze
(74) *Attorney, Agent, or Firm* — McAndrews, Held & Malloy, Ltd.

(57) ABSTRACT

An example remote control for a radiographic source includes: a forward cable section configured to extend into and through a radiographic source housing, to expose a radiographic source to an exterior of the housing, and to retract into and through the radiographic source housing to retract the radiographic source into the radiographic housing; a drive cable section coupled to the forward cable section; and a drive gear configured to extend the forward cable section by driving the drive cable section in a first direction, and to retract the forward cable section by driving the drive cable section in a second direction, wherein the forward cable has a smooth exterior surface to have a lower friction than the drive cable section while traversing the radiographic source housing.

18 Claims, 5 Drawing Sheets

(58) Field of Classification Search
CPC ........... A61B 6/542; A61B 6/588; A61B 6/08; A61B 6/00; A61B 6/502; A61B 6/54; A61B 6/4488; A61B 6/4429; A61B 6/548; A61B 6/4464; A61B 6/56; A61B 6/145; A61B 6/4266; A61B 6/4441; A61B 6/487; A61B 6/4283; A61B 6/464; A61B 6/52; A61B 6/469; A61B 6/462; A61B 6/14; A61B 6/563; G21G 4/06; G21F 5/015; G21F 3/00; G21F 1/125; G21F 1/106; A61N 5/1002; A61N 2005/1003; A61N 2005/1004; A61M 2025/0063; G01N 23/18; G01N 23/046; G01N 23/04; G01N 2223/631; G01N 2223/646; G03B 42/02; G01T 1/00; G01T 1/02; G21K 1/046; H01J 35/00; H01J 35/106; H01J 19/54; H01J 19/74; H01J 35/16; H01J 7/26; H01J 37/165; H01J 19/36; G01V 5/0016; G01V 5/0066; G01V 5/005; G01V 5/0058
USPC .................... 378/91, 101, 102, 196–198, 194
See application file for complete search history.

METHODS AND APPARATUS FOR CONTROL OF RADIOGRAPHIC SOURCE EXPOSURE

The present application claims the benefit of U.S. Provisional Patent Application Ser. No. 63/106,664, filed Oct. 28, 2020, entitled "METHODS AND APPARATUS FOR CONTROL OF RADIOGRAPHIC SOURCE EXPOSURE." The entirety of U.S. Provisional Patent Application Ser. No. 63/106,664 is expressly incorporated herein by reference.

BACKGROUND

This disclosure relates generally to radiography and, more particularly, to methods and apparatus for control of radiographic source exposure.

Industrial radiography is often used for producing images of objects that are otherwise difficult to inspect, and involves exposing a source of high-energy radiation (e.g., gamma rays) and collecting penetrating and/or reflected rays to form a radiographic image. When not in use, gamma ray sources, such as radioactive isotopes, are stored in shielding devices.

SUMMARY

Methods and apparatus for control of radiographic source exposure are disclosed, substantially as illustrated by and described in connection with at least one of the figures, as set forth more completely in the claims.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Wherever appropriate, similar or identical reference numerals are used to refer to similar or identical components.

DETAILED DESCRIPTION

For the purpose of promoting an understanding of the principles of the claimed technology and presenting its currently understood, best mode of operation, reference will be now made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would typically occur to one skilled in the art to which the claimed technology relates.

Disclosed example remote controls for radiographic sources include: a forward cable section configured to extend into and through a radiographic source housing, to expose a radiographic source to an exterior of the housing, and to retract into and through the radiographic source housing to retract the radiographic source into the radiographic housing; a drive cable section coupled to the forward cable section; and a drive gear configured to extend the forward cable section by driving the drive cable section in a first direction, and to retract the forward cable section by driving the drive cable section in a second direction, wherein the forward cable has a smooth exterior surface to have a lower friction than the drive cable section while traversing the radiographic source housing.

Some example remote controls further include a cable connector configured to mechanically couple the forward cable section to the drive cable section. In some example remote controls, the forward cable section and the drive cable section have respective lengths such that the cable connector and the forward cable section do not come into contact with the drive gear. In some example remote controls, the forward cable section and the drive cable section have respective lengths such that the cable connector does not enter the radiographic source housing. Some example remote controls further include a drive gear housing configured to contain the drive gear, the drive gear housing having a window configured to enable viewing of the cable connector when the forward cable section is at a predetermined position within the drive gear housing. In some example remote controls, the cable connector is configured to be detachable from at least one of the forward cable section or the drive cable section.

In some example remote controls, the forward cable section and the drive cable section have respective lengths such that the drive cable section does not enter the radiographic source housing. In some example remote controls, the forward cable section includes at least one of a semi-rigid spring steel, a spiral wound cable, a close-wound cable, or a compacted wire rope. In some example remote controls the forward cable section includes an outer coating configured to have less than a threshold coefficient of friction. In some example remote controls, the outer coating comprises at least one of Polytetrafluoroethylene (PTFE), molybdenum disulfide (MoS2) lubricants, graphite, Xylan®-brand fluoropolymer-based coatings, EthyleneChloroTrfluoroEthylene (ECTFE), Canadize-brand lubricants, or parylene.

Some example remote controls further include a handle configured to actuate the drive gear. Some example remote controls further include a motor configured to actuate the drive gear. Some example remote controls further include: a control conduit configured to cover portions of the forward cable section and the drive cable section located between the drive gear and the radiographic source housing; and a source connector configured to secure the control conduit to the radiographic source housing. In some example remote controls the forward cable section is configured to traverse an S-shaped source tube within the radiographic source housing to push the radiographic source through the S-shaped source tube to an outlet of the S-shaped tube.

Disclosed example methods to control exposure of a radiographic source involve: mechanically coupling a forward cable section to a radiographic source within a radiographic source housing; and extending the radiographic source to an exterior of the radiographic source housing from an interior of the housing to expose the radiographic source, by driving the forward cable section using a drive cable section, wherein the forward cable has a smooth exterior surface to have a lower friction than the drive cable section while traversing the radiographic source housing.

In some example methods, the extending the radiographic source involves turning a drive gear in a first direction to drive the drive cable section to thereby drive the forward cable section. Some example methods further involve retracting the radiographic source into the radiographic source housing by turning the drive gear in a second direction to drive the drive cable section to thereby retract the radiographic source via the forward cable section and the drive cable section. Some example methods further involve attaching the forward cable section to the drive cable section via a cable connector. Some example methods further involve attaching the forward cable section to the radiographic source. In some example methods, the extending of the radiographic source ends prior to the drive cable section entering the radiographic source housing.

Figure 1A:
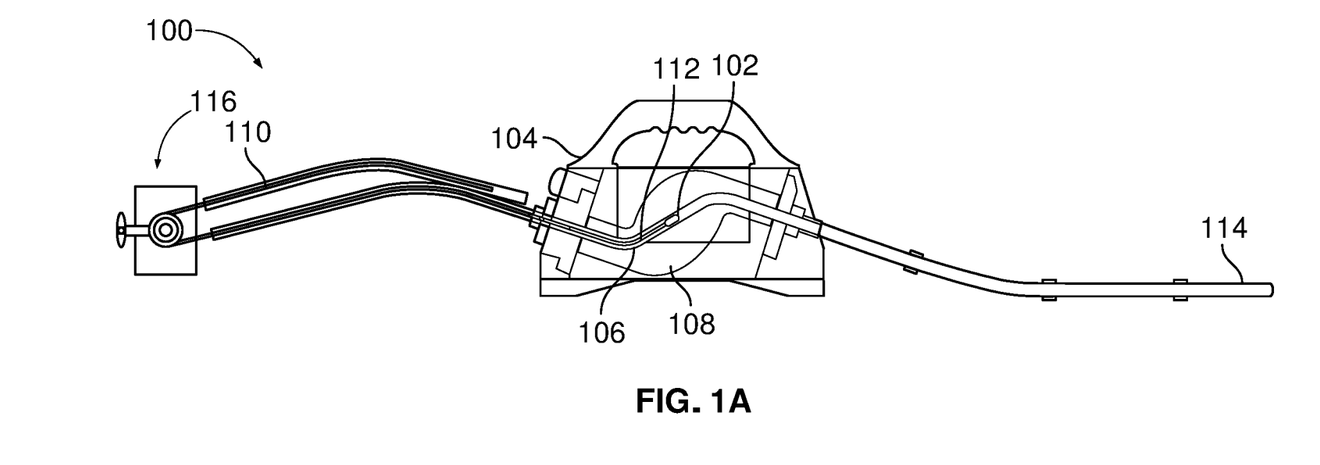
FIGS. 1A and 1B illustrate example radiographic system for providing radiation for radiography, in accordance with aspects of this disclosure.
Figure 1B:
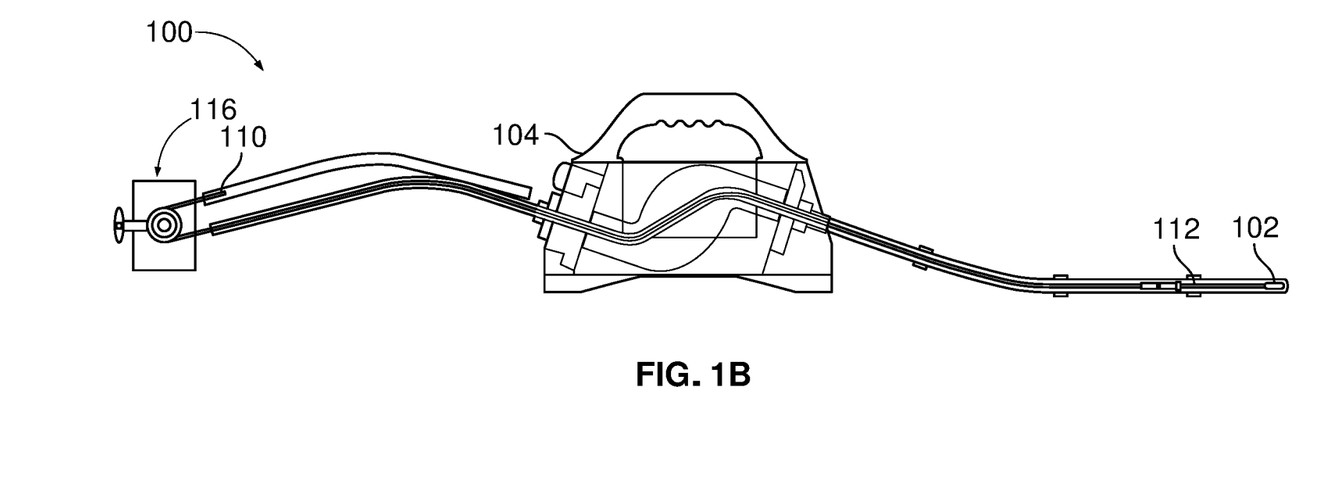

FIGS. 1A and 1B illustrate example radiographic system 100 for providing radiation for radiography. The radiographic system 100 of FIG. 1 includes a radiographic source 102 which is contained within a radiographic source housing 104. The example radiographic source 102 is a mass of radioactive material which emits radiation (e.g., X-rays and/or gamma rays) due to decay of the material.

The radiographic source housing 104 includes an S-shaped source tube 106 within a shield 108. The source tube 106 provides a pathway for the radiographic source 102 to be exposed to an exterior of the shield 108 and retracted to a shielded position within the interior of the shield 108. FIG. 1A illustrates the radiographic source 102 in the shielded position, and FIG. 1B illustrates the radiographic source in an exposed position.

To control the position of the radiographic source 102, the radiographic source housing 104 enables connection of a control cable 110 to the radiographic source 102 for exposure and retraction of the radiographic source 102. The control cable 110 may be physically attached or connected to a pigtail connector 112 that is physically coupled to the radiographic source 102.

When engaged, the control cable 110 is controlled to extend into and through the source tube 106 to push the radiographic source 102 to an exposed position external to the radiographic source housing 104. Conversely, the control cable 110 is retracted to pull the radiographic source 102 from the exposed position back into the source tube 106 to the shielded position, at which time the control cable 110 may be detached from the radiographic source 102.

In the system 100 of FIG. 1, the exposed position of the radiographic source 102 may be controlled by a guide tube 114, through which the radiographic source 102 travels as the source 102 is pushed by the control cable 110. The control cable 110 has sufficient column strength to push the radiographic source 102 through the source tube 106 and through the guide tube 114.

The control cable 110 is controlled by a remote control 116. The remote control 116 physically engages the control cable 110 to advance or retract the control cable 110 relative to the remote control 116.

Figure 2:
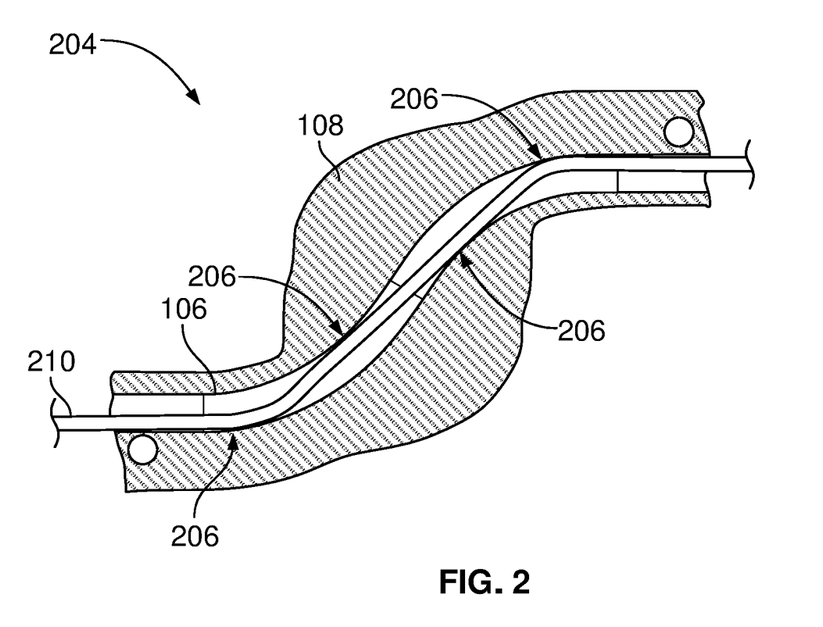
FIG. 2 is a cross-section of a conventional radiographic source and radiographic source housing in which portions of the radiographic source housing are subject to undesirable mechanical wear during use.

FIG. 2 is a cross-section of a conventional radiographic source shield assembly 204 in which portions of the radiographic source shield assembly 204 are subject to undesirable mechanical wear during use. As illustrated in FIG. 2, the source tube 106 extends through the shield 108 in an S-shaped curve. As a result, there are multiple points 206 in the source tube 106 at which substantial friction occurs between the control cable 110 and the source tube 106 as a conventional control cable 210 advances and retracts through the source tube 106.

Conventional control cables (also referred to as drive cables) are not purpose-built for source actuation in radiography applications. While radiography systems are designed to be sealed when assembled, radiography systems are effectively unsealed during setup, breakdown, and/or improper storage, which permits exposure to contaminants (e.g., dirt, sand, water) for which the radiography systems were not designed.

The conventional control cable 210 is a flexible steel cable with a helical outer winding. The helical outer winding enables the remote control 116 to engage the conventional control cable 210 and advance and retract the cable 210 with a high degree of precision. However, when not properly maintained, the helical outer windings can create substantial friction and/or abrasion at the points 206 on the interior of the source tube 106 as the conventional control cable 210 traverses the S-shaped curve. The friction and/or abrasion may create premature wear in the source tube 106 and reduce the useful life of the radiographic source shield assembly 204 and/or the radiographic source housing 104. When the control cable 110 is not provided with sufficient cable lubrication, the friction and/or abrasion may also result in increased risk of failure of the control cable 110.

Figure 3A:
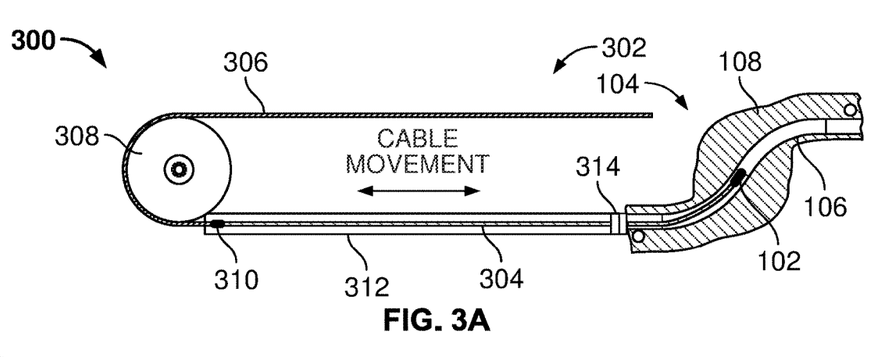
FIGS. 3A and 3B illustrate an example radiographic system that may be used to implement the radiographic system of FIGS. 1A and 1B, in which a remote control device used to control exposure of the radiographic source subjects the radiographic source housing to substantially less wear than in conventional systems.
Figures 3B, 4:
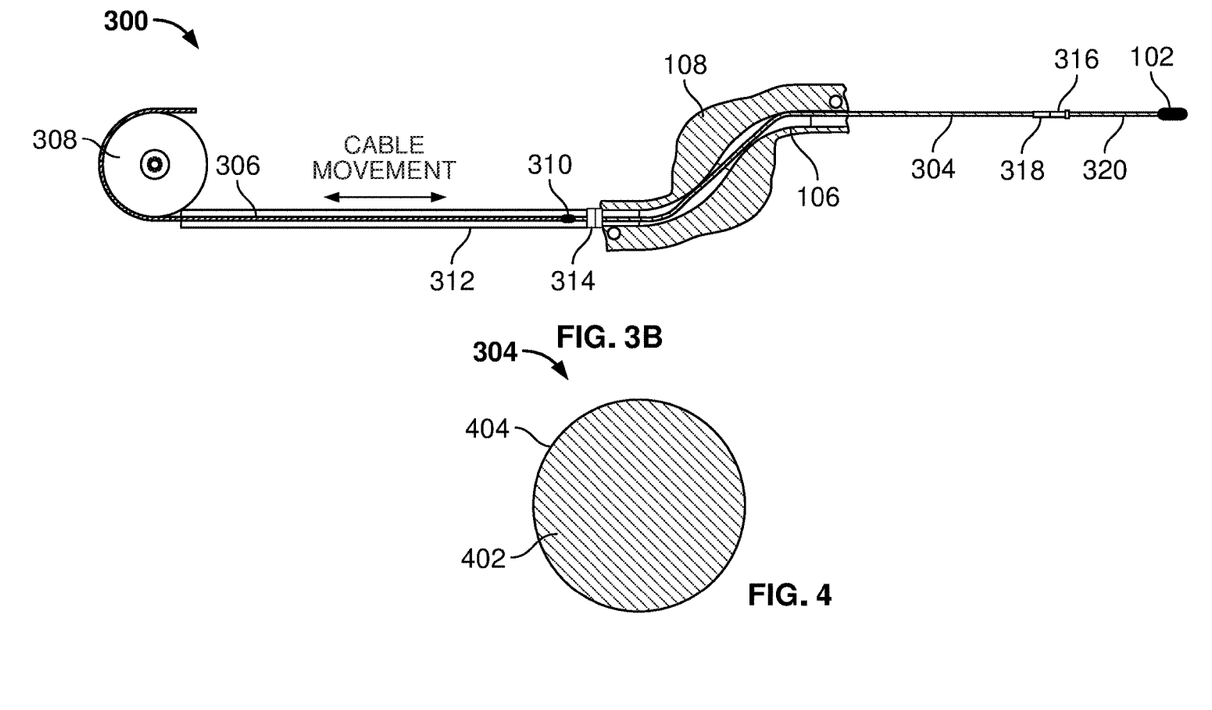
FIG. 4 is a cross-section of the example forward cable section of FIGS. 3A and 3B.

FIGS. 3A and 3B illustrate an example radiographic system 300 that may be used to implement the radiographic system 100 of FIGS. 1A and 1B, in which a remote control device 302 used to control exposure of the radiographic source 102 subjects the radiographic source housing 104 to substantially less wear than in conventional systems (e.g., the conventional system of FIG. 2).

In contrast with the conventional control cable 210 of FIG. 2, the example remote control device 302 of FIG. 3A includes a forward cable section 304 configured to extend into and through the radiographic source housing 104, and a drive cable section 306 coupled to the forward cable section 304.

The drive cable section 306 may be similar or identical to the conventional control cable 210 of FIG. 2. In contrast, the forward cable section 304 has a smooth exterior surface, such that the forward cable section 304 has a lower friction than the drive cable section 306 (or the conventional control cable 210) while traversing the radiographic source housing 104 (e.g., through the source tube 106). FIG. 4 is a cross-section of the example forward cable section 304 of FIGS. 3A and 3B. For example, the forward cable section 304 may include an interior column 402 constructed using one or more of a semi-rigid spring material, a spiral wound cable, a close-wound cable, and/or a compacted wire rope. The interior column 402 may be a metal, a polymer, and/or any other material that has acceptable flexibility and is capable of linear actuation while maintaining sufficient strength in a radioactive environment for at least a threshold life span.

The interior column 402 may be wrapped, coated, or otherwise covered by an outer cover 404 (e.g., a coating, a physical cover, a wrap, etc.) that has less than a threshold coefficient of friction. In some examples, the outer coating is a tape, wrap, coating, and/or other covering, and may be constructed from Polytetrafluoroethylene (PTFE), molybdenum disulfide ($MoS_2$) lubricants (sold by DuPont under the MolyKote® brand), graphite, Xylan®-brand fluoropolymer-based coatings (sold by Whitford Corporation), EthyleneChloroTrfluoroEthylene (ECTFE), Canadize-brand lubricants (sold by General Magnaplate), and/or parylene. However, any other appropriate material may be used as a coating. In some examples, a material may be chosen or modified to visibly show wear in the coating of the forward cable section 304. As a result of the lower friction, the forward cable section 304 substantially reduces or eliminates abrasion and/or wear on the source tube 106 while advancing and retracting the radiographic source 102.

The drive cable section 306 engages a drive gear 308 of the remote control device 302. The drive gear 308 extends the forward cable section 304 (and the radiographic source 102) by driving the drive cable section 306 in a first direction, and retracts the forward cable section 304 (and the radiographic source 102) by driving the drive cable section in a second direction, while the forward cable section 304 does not come into contact with the drive gear 308.

A cable connector 310 mechanically couples the forward cable section 304 to the drive cable section 306. In the example of FIGS. 3A and 3B, only the drive cable section 306 engages with the drive gear 308. The forward cable section 304 and the drive cable section 306 have respective lengths such that the cable connector 310 and the forward cable section 304 do not come into contact with the drive gear 308. Similarly, the forward cable section 304 and the drive cable section 306 have respective lengths such that the cable connector 310 and the drive cable section 306 do not enter the radiographic source housing 104 and/or do not enter the source tube 106.

The example remote control device 302 includes a control conduit 312 to cover the forward cable section 304 and/or the drive cable section 306 at least between the drive gear 308 and the radiographic source housing 104. In the example of FIGS. 3A and 3B, the control conduit 312 is coupled to a conduit connector 314 that secures the control conduit 312 to the radiographic source housing 104 and aligns an outlet of the control conduit 312 with a corresponding inlet of the radiographic source housing 104. For example, the forward cable section 304 and a forward connector 318 may be connected to the radiographic source 102 via a pigtail connector 316 and a pigtail cable 320. Once connected, the conduit connector 314 can be connected to the radiographic source housing 104 and secured, the forward cable section 304 may be physically attached to the pigtail cable 320 affixed to the radiographic source 102. In some examples, the pigtail cable 320 is made of the same or similar construction as the forward cable section 304 or the same or similar construction as the drive cable section 306.

The example conduit connector 314 may be implemented using conventional connectors used with the Sentinel 880 Gamma Ray Source Projection system, sold by QSA Global, Inc., of Burlington, Mass.

The disclosed example remote control, including the forward cable section 304, has the advantage that the forward cable section 304 reduces overall sliding friction with the source tube 106, relative to the conventional control cable 210. The reduction in sliding friction extends the useful life of the source tube 106 by extending the time and usage required to wear through the tube and into the shield 108, which may be depleted uranium, adjacent to the source tube 106. This increase in useful life of the source tube 106 is a substantial financial benefit for the owners of the system.

Figure 5A:
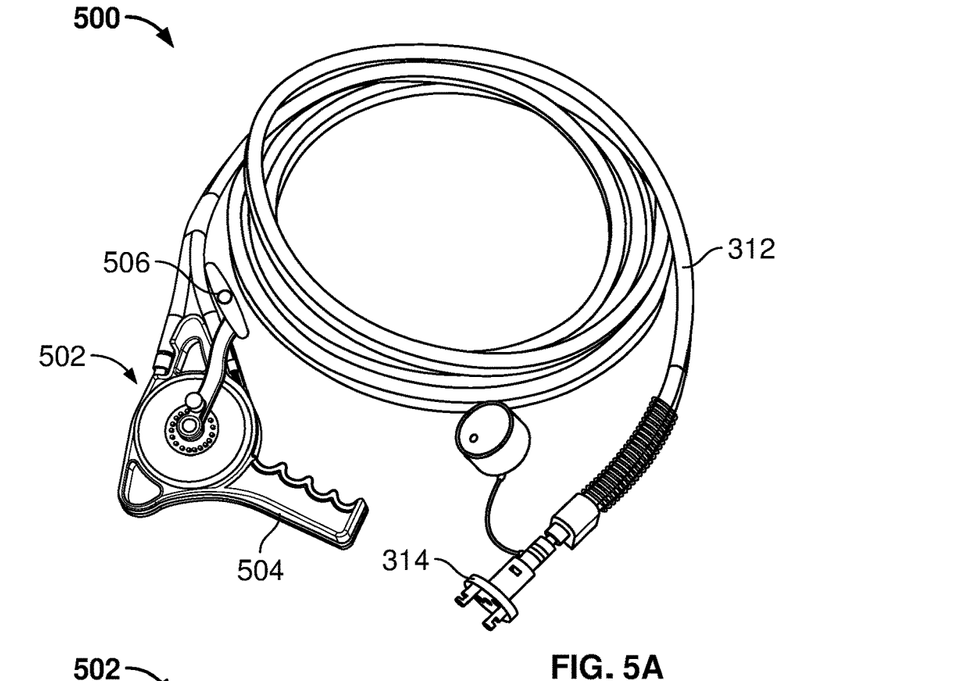
FIG. 5A illustrates an example manual remote control configured to implement the radiographic system of FIGS. 3A and 3B.

FIG. 5A illustrates an example manual remote control 500 configured to implement the radiographic system 300 of FIGS. 3A and 3B. The manual remote control 500 includes a pistol-style housing 502 that houses the drive gear 308. The housing 502 includes a grip 504, which may be grasped by an operator of the remote control 500 when turning a handle 506 attached to the drive gear 308. Turning the handle 506 in an exposure (e.g., advancement) direction causes the drive gear 308 to advance the drive cable section 306 toward the conduit connector 314, which causes the forward cable section 304 to similarly advance and push the radiographic source 102. Conversely, turning the handle 506 in a retraction direction (opposite the exposure direction) causes the drive gear 308 to retract the drive cable section 306 away from the conduit connector 314, which pulls the forward cable section 304 to retract the radiographic source 102 toward the shielded or storage position within the source tube 106.

Figure 5B:
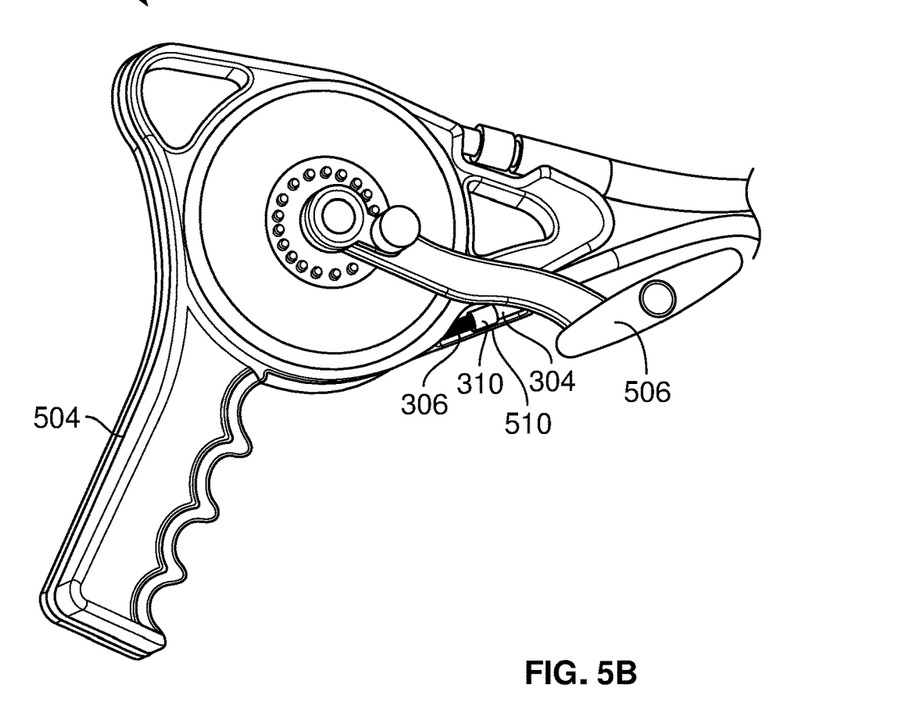
FIG. 5B is a more detailed view of the example manual remote control of FIG. 5A, including a window through which the condition of the cable connector of FIGS. 3A and 3B may be observed without exposure of the cable connector to the exterior of the manual remote control.

FIG. 5B is a more detailed view of the example manual remote control 500 of FIG. 5A, including a window 510 through which the condition of the cable connector of FIGS. 3A and 3B may be observed without exposure of the cable connector to the exterior of the manual remote control.

While FIGS. 5A and 5B illustrate a pistol-style housing, reel-style housings and/or any other type of housing may be used. Additionally or alternatively, the drive gear 308 may be replaced with a different type of actuator and/or drive interface to drive the drive cable section 306 and/or the forward cable section 304. In some examples, the drive gear 308 (or other drive interface) may be automatically actuated (e.g., via a motor) instead of manually actuated via a handle.

Figure 6:
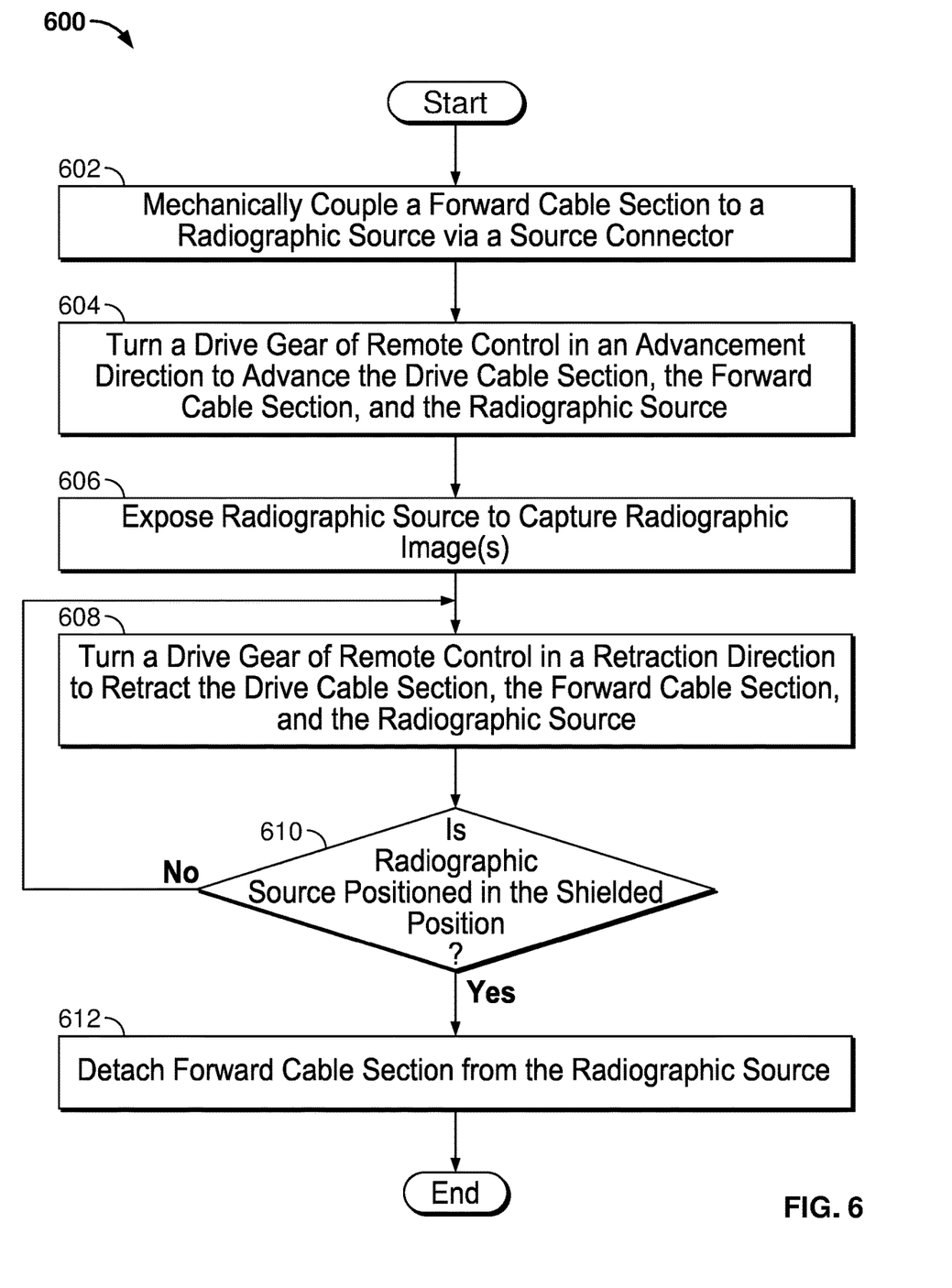
FIG. 6 is a flowchart representative of an example method which may be performed to control exposure of a radiographic source using the system of FIGS. 3A and 3B.

FIG. 6 is a flowchart representative of an example method 600 which may be performed to control exposure of a radiographic source 102 using the system of FIGS. 3A and 3B. While the method 600 is disclosed below with reference to certain applicable elements, local regulations may require that additional actions or steps, such as (but not limited to) confirmatory surveys of radiation levels prior to and/or after exposure of the radioactive source, be taken in conjunction with the disclosed steps.

At block 602, the forward cable section 304 is mechanically coupled to a radiographic source 102 via a conduit connection. For example, the forward cable section 304 may be mechanically attached to the pigtail connector 316 via the forward connector 318, and/or the control conduit 312 may be coupled to the radiographic source housing 104.

At block 604, the drive gear 308 is turned in an advancement direction to advance the drive cable section 306. As a result of advancing the drive cable section 306, the forward cable section 304 and the radiographic source 102 are returned to the stored position within the shield 108.

At block 606, the radiographic source 102 is exposed for a threshold time period to capture one or more radiographic image(s) (e.g., via a radiation detector or imager).

At block 608, the drive gear 308 is turned in a retraction direction to retract the drive cable section 306. As a result of retracting the drive cable section 306, the forward cable section 304 and the radiographic source 102 are retracted to secure the radiographic source 102.

At block 610, it is determined whether the radiographic source 102 is secured in the shielded position. If the radiographic source 102 has not been secured in the shielded position (block 610), the method 600 returns to block 608 to continue retraction.

When the radiographic source 102 is positioned in the shielded position (block 610), at block 612 the forward cable section 304 may be detached from the radiographic source 102. The example method 600 then ends.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A remote control for a radiographic source, the remote control comprising:
   a forward cable section configured to:
      detachably couple to a radiographic source via a connector;
      extend into and through a radiographic source housing to expose a radiographic source to an exterior of the housing; and
      retract into and through the radiographic source housing to retract the radiographic source into the radiographic housing;
   a drive cable section coupled to the forward cable section;
   a cable connector configured to mechanically couple the forward cable section to the drive cable section; and
   a drive gear configured to extend the forward cable section by driving the drive cable section in a first direction, and to retract the forward cable section by driving the drive cable section in a second direction, wherein the forward cable has a smooth exterior surface to have a lower friction than the drive cable section while traversing the radiographic source housing.

2. The remote control of claim 1, wherein the forward cable section and the drive cable section have respective lengths such that the cable connector and the forward cable section do not come into contact with the drive gear.

3. The remote control of claim 1, wherein the forward cable section comprises at least one of a semi-rigid spring steel, a spiral wound cable, a close-wound cable, or a compacted wire rope.

4. The remote control of claim 1, wherein the forward cable section comprises an outer coating configured to have less than a threshold coefficient of friction.

5. The remote control of claim 4, wherein the outer coating comprises at least one of Polytetrafluoroethylene (PTFE), molybdenum disulfide ($MoS_2$) lubricants, graphite, Xylan®-brand fluoropolymer-based coatings, EthyleneChloroTrfluoroEthylene (ECTFE), Canadize-brand lubricants, or parylene.

6. The remote control of claim 1, further comprising a handle configured to actuate the drive gear.

7. The remote control of claim 1, further comprising a motor configured to actuate the drive gear.

8. The remote control of claim 1, further comprising:
   a control conduit configured to cover portions of the forward cable section and the drive cable section located between the drive gear and the radiographic source housing; and
   a source connector configured to secure the control conduit to the radiographic source housing.

9. The remote control of claim 1, wherein the forward cable section is configured to traverse an S-shaped source tube within the radiographic source housing to push the radiographic source through the S-shaped source tube to an outlet of the S-shaped tube.

10. A remote control for a radiographic source, the remote control comprising:
   a forward cable section configured to extend into and through a radiographic source housing, to expose a radiographic source to an exterior of the housing, and to retract into and through the radiographic source housing to retract the radiographic source into the radiographic housing;
   a drive cable section coupled to the forward cable section, wherein the forward cable section and the drive cable section have respective lengths such that the cable connector does not enter the radiographic source housing;
   a cable connector configured to mechanically couple the forward cable section to the drive cable section; and
   a drive gear configured to extend the forward cable section by driving the drive cable section in a first direction, and to retract the forward cable section by driving the drive cable section in a second direction, wherein the forward cable has a smooth exterior surface to have a lower friction than the drive cable section while traversing the radiographic source housing.

11. The remote control of claim 10, further comprising a cable connector configured to mechanically couple the forward cable section to the drive cable section.

12. The remote control of claim 11, further comprising a drive gear housing configured to contain the drive gear, the drive gear housing having a window configured to enable viewing of the cable connector when the forward cable section is at a predetermined position within the drive gear housing.

13. The remote control of claim 11, wherein the cable connector is configured to be detachable from at least one of the forward cable section or the drive cable section.

14. A method to control exposure of a radiographic source, the method comprising:
   mechanically coupling a forward cable section to a radiographic source within a radiographic source housing; and
   extending the radiographic source to an exterior of the radiographic source housing from an interior of the housing to expose the radiographic source, by driving the forward cable section using a drive cable section, wherein the forward cable has a smooth exterior surface to have a lower friction than the drive cable section while traversing the radiographic source housing wherein the extending the radiographic source ends prior to the drive cable section entering the radiographic source housing.

15. The method of claim 14, wherein the extending the radiographic source comprises turning a drive gear in a first direction to drive the drive cable section to thereby drive the forward cable section.

16. The method of claim 15, further comprising retracting the radiographic source into the radiographic source housing by turning the drive gear in a second direction to drive the drive cable section to thereby retract the radiographic source via the forward cable section and the drive cable section.

17. The method of claim 14, further comprising attaching the forward cable section to the drive cable section via a cable connector.

18. The method of claim 14, further comprising attaching the forward cable section to the radiographic source.

* * * * *